United States Patent [19]

Wu

[11] Patent Number: 4,668,805
[45] Date of Patent: May 26, 1987

[54] CHROMONES

[75] Inventor: Edwin S. Wu, Rochester, N.Y.

[73] Assignee: Pennwalt Corporation, Philadelphia, Pa.

[21] Appl. No.: 885,517

[22] Filed: Jul. 14, 1986

Related U.S. Application Data

[63] Continuation-in-part of Ser. No. 441,893, Nov. 15, 1982, abandoned, which is a continuation-in-part of Ser. No. 259,387, May 1, 1981, abandoned, Ser. No. 259,403, May 1, 1981, abandoned, and Ser. No. 330,122, Dec. 14, 1981, abandoned.

[51] Int. Cl.$^4$ .............................................. C07D 311/36
[52] U.S. Cl. ..................................................... 549/403
[58] Field of Search .......................................... 549/403

[56] References Cited

U.S. PATENT DOCUMENTS 4,391,821 7/1983 Korbonits et al. .................. 549/401

OTHER PUBLICATIONS

Wang et al., Acta Pharm. Sinica, 15, 253 (1980).
Da Re et al., J. Med. Chem., 15, 868 (1972).

Primary Examiner—Nicky Chan

[57] ABSTRACT

Chromone derivatives such as 7-(3-n-propylamino-2-hydroxypropoxy)-2,3-diphenylchromones which are useful as pharmaceuticals having antihypertensive properties.

10 Claims, No Drawings

CHROMONES

BACKGROUND OF THE INVENTION

This is a continuation-in-part of my copending application U.S. Ser. No. 441,893 filed Nov. 15, 1982, now abandoned; which in turn was a continuation-in-part of my copending applications, U.S. Ser. No. 259,387, U.S. Ser. No. 259,403 both filed May 1, 1981 and both now abandoned; and U.S. Ser. No. 330,122, filed Dec. 14, 1981, now abandoned.

This invention relates to chromone derivatives substituted by 3-amino-2-hydroxypropoxy side chains, medicinal preparations containing the same, and the utilization of such preparations as antihypertensive agents in animals.

Compounds related to propranolol, a potent beta-blocker, constitute a large class of compounds which have profound effects on the cardiovascular system and have found utility as antihypertensive, antidysrhythmic and antianginal drugs. However, the beta-blocking properties of these compounds are often undesirable, especially in patients with coronary insufficiencies and bronchial diseases. A compound devoid of beta-blocking effect but retaining antihypertensive effect on the blood pressure of warm-blooded animals has therefore long been sought.

Several patents disclose various compounds which either have beta-blocking properties or do not have antihypertensive effects. U.S. Pat. No. 3,891,651 discloses compounds which are amides and, it is thought, the nitrogen of the amide which is contained in the isoquinoline fragement is likely to be responsive for any activity in that compound. U.S. Pat. No. 3,816,470 discloses various salts of secondary amines with chromone-2-carboxylic acids. U.S. Pat. No. 3,812,156 discloses a method of preparing ethyl flavone-7-oxyacetate. U.S. Pat. No. 3,352,754 discloses simple 7-hydroxy or 7-alkoxy isoflavones which are not amines and which are used for various inflammatory disorders. U.S. Pat. No. 3,219,531 discloses 5,7-dioxyacetic acid flavone compounds, but no amine functions are present. U.S. Pat. No. 3,046,275 discloses 7-dialkylaminoalkoxy derivatives but does not contain any of the hydroxyl groups of the side chain which is central for activity. Various monodialkylaminoethyl ethers of quercetin are disclosed in U.S. Pat. No. 2,861,992, but do not contain 3-amino-2-hydroxypropoxy side chains. Also not containing that side chain are the compounds disclosed in U.S. Pat. No. 2,897,211.

P. Da Re et al., *J. Med. Chem.*, Vol. 15, 868–869 (1972), describe the testing of chromones for betaadrenergic blocking activity. Da Re et al. found that all the compounds were devoid of beta-blocking activity, suggesting that chromones would not be expected to have antihypertensive properties. Additionally, ethanol-amine analogues of the Da Re et al. materials are disclosed in Vol. 15 pages 198–199 of the *J. Med. Chem.*, (1972). These analogues are beta-blockers, typical of the pronethalol type which owe their activity to the 2-isopropylaminoethanol side chain. Typical 3-amino-2-hydroxypropoxy side chain furochromone compounds are disclosed in papers presented in *Drugs of the Future*, Vol. III, No. 8 (1978), pages 569–571; *Drugs of the Future*, Vol. III, No. 11, (1978), pages 816–818; and *Therapie*, (1977), Vol. 32, pages 111–120. None of these references, of course, even suggest that antihypertensive activity may be possible with or without beta-blockade.

None of these references disclose the compounds of this invention.

Several flavones are disclosed in an article published in *Acta Pharmaceutica Sinica*, 15 253 (1980) in the People's Republic of China, where lack of beta-blocking is reported. There is no suggestion that such compounds have antihypertensive properties.

SUMMARY OF THE INVENTION

The present invention provides a diphenylchromone of the formula:

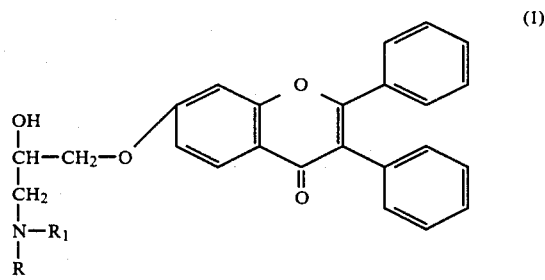

(I)

or a pharmaceutically acceptable salt thereof wherein R is hydrogen or lower alkyl and $R_1$ is hydrogen, lower alkyl, lower cycloalkyl or lower alkenyl. By "lower" is meant that the relevant group contains no more than about six carbon atoms.

These compounds are useful as antihypertensive agents in the treatment of warm-blooded animals.

The compounds are usually mixed with a pharmaceutical carrier so that the composition for commercial use contains 0.5 to 20% by weight of the compound.

The compositions are normally adapted for peroral or parenteral use, but may be used in other forms such as suppositories. The peroral compositions are preferably in the form of tablets, capsules or suspensions, while the parenteral composition is preferably an injectable solution or suspension.

Examples of suitable inert pharmaceutical carriers are celluloses (particularly microcrystalline celluloses), sugar syrups, potato starch, talcum, polyethylene glycols and lactose.

Examples of suitable acids for forming the acid addition salts are maleic acid, hydrochloric acid, sulfuric acid, phosphoric acid, methanesulfonic acid, tartaric acid, citric acid, and the cation exchange resins such as the carboxylic acid, phosphonic acid and sulfonic acid resins.

For sustained release, a coated complex of the compound absorbed onto an ion exchange resin may be employed in accordance with the teaching of British Pat. No. 1,544,761.

The usual peroral dosage of the compound is 0.1 to 150 mg. per day (preferably 0.1 to 50 mg.) while the parenteral dosage is normally 0.1 to 40 mg. per day (preferably 0.1 to 10 mg.)

The capsules, tablets, syrups and suspensions of the compounds are prepared by conventional procedures.

It should be noted that the compounds of this invention are antihypertensive agents, not hypotensive agents, i.e., they reduce the blood pressure to normal but not below normal.

DETAILED DESCRIPTION

The compounds of formula (1) above can be prepared by reacting epichlorohydrin or epibromohydrin with a compound of the formula

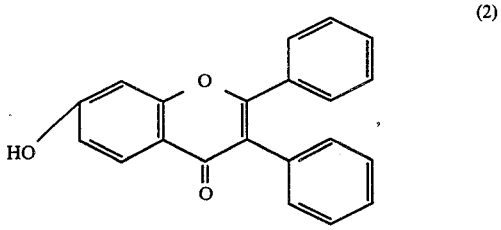
(2)

in the presence of a solvent and a base to give a product where the hydrogen of the hydroxyl group of formula (2) is substituted by

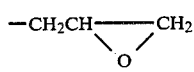

This epoxide is allowed to react with ammonia or an amine, e.g., $RNH_2$ where R and $R_1$ are as above defined, in an alcoholic solvent at elevated temperature to afford a product of formula (1).

The following general procedures are used in the examples to follow:

A. For Epoxides

Epichlorohydrin or epibromohydrin (greater than 2 equivalents) is added in the presence or absence of nitrogen to a stirred solution or suspension of the hydroxy chromone derivative in solvents, such acetone, aqueous ethanol, 50% aqueous dimethylsulfoxide (DMSO) or water, containing a suitable base, such as potassium carbonate or sodium hydroxide, with or without sodium iodide. The reaction is allowed to proceed either at room temperature or elevated temperature and monitored by thin layer chromatography (tlc). The product, formed as solid, is then collected and washed with water. The mother liquor is diluted with water and extracted with chloroform ($CHCl_3$) to give more product. Where the product is soluble in solvents, the reaction mixture is filtered off and the solids washed with the solvent. The filtrate is evaporated to give a solid which is washed with water to get rid of remaining traces of the base. Yield is in the 60 to 80% range. This material is usually used directly for further reaction without purification.

B. For Epoxide Ring-Opening With Amine and the Amine Salt Formation

A white suspension of the chromone epoxide, an amine (such as a low (large excess) or a high (10% excess) boiling point amine) an alcoholic solvent (such as methanol (A.R.) ethanol (abs.) or isopropyl alcohol) is heated at elevated temperatures until the starting material is gone (as followed by tlc). Since the reaction product is usually soluble in the alcohol, the precipitate is filtered off and the filtrate is evaporated to give a viscous liquid which, upon addition of anhydrous ether or alcohol, crystallizes out. When the product is insoluble in alcohol at the end of the reaction, it is collected. Purification of the amine derivative is performed via acid-base work-up, column chromatography or recrystallization. The amine obtained is either suspended or dissolved in an alcohol, and then acidified with an alcohol solution saturated with hydrogen chloride or other acid to a pH of 1. The salt formed is precipitated out directly or by addition of anhydrous ether. The salt is then recrystallized from suitable solvents.

EXAMPLE 1

Preparation of 7-(2-hydroxy-3-isopropylaminopropoxy)-2,3-diphenylchromone hydrochloride

7-(2,3-Epoxypropoxy)-2,3,-diphenylchromone

To a solution of 50% aqueous DMSO (280 ml), containing sodium hydroxide (5.60 g, 140 mmol) was added 7-hydroxy 2,3,-diphenylchromone (44.01 g, 140 mmol) and the resultant mixture was stirred until most of the solid went into the solution. Epichlorohydrin was then introduced into the suspension. The solution was stirred at room temperature (RT) for 2.5 days and solid formed during the reaction was collected from time to time (about twice a day). The white solid (total=47.58 g) was recrystallized from isopropyl alcohol several times to afford 28.15 g of relatively pure white prisms, m.p. 143°–145°; yield 54%. The mother liquor was concentrated to produce more crystals.

7-[2-Hydroxy-3-(isopropylamino)propoxy]-2,3-diphenylchromone hydrochloride

A white suspension of relatively pure 7-(2,3-epoxypropoxy)-2,3-diphenylchromone (27.78 g, 75 mmol), isopropylamine (18.8 ml), and methanol (A. R., 150 ml) was heated under nitrogen at 55° C. until complete disappearance of the starting epoxide. The white precipitate (1.09 g) in the cooled reaction mixture was filtered off, and the filtrate was evaporated to a golden syrup. Anhydrous ether was added, and white crystals (28.07 g) were obtained. It was column-chromatographed over silica gel. This purification yielded 24.05 g of white crystals, m.p. 152°–154° (75%).

The amine thus obtained was dissolved in 100 ml of MeOH A. R. and treated with saturated solution of hydrogen chloride in ethanol until the solution was pH=1. The hydrochloride salt was precipitated out by addition of anhydrous ether. A white solid was collected and recrystallized from MeOH-ether (also decolorized with a small amount of activated charcoal) to produce 21.6 g (83% yield) of pure white crystals, m.p. 164°–166°.

Anal. Calc'd. for $C_{27}H_{28}ClNO_4.H_2O$: C, 67.00; H, 6.25; Cl, 7.32; N, 2.89.

Found: C, 67.10; H, 5.95; Cl, 7.19; N, 2.65.

EXAMPLE 2

Preparation of 7-(3-n-propylamino-2-hydroxypropoxy)-2,3-diphenylchromone hydrochloride The free base was prepared according to Method B from n-propylamine and 7-(2,3-epoxypropoxy)-2,3-diphenylchromone in 65% yield as white prisms, m.p. 140°–142° (iPrOH).

The hydrochloride salt was obtained in 95% yield as white prisms, m.p. 134°–136° (iPrOH)

EXAMPLE 3

Preparation of 7-(3-cyclopropylamino-2-hydroxypropoxy)-2,3-diphenylchromone

The amine was prepared according to Method B from cyclopropylamine and 7-(2,3-epoxypropoxy)-2,3-diphenylchromone and purified by high pressure liquid chromatography to give white crystals, m.p. 135°–137° (MeOH-ether), in 25% yield.

EXAMPLE 4

Preparation of 7-(3-allylamino-2-hydroxypropoxy)-2,3-diphenylchromone

Using Method B, the reaction of 7-(2,3-epoxypropoxy)-2,3-diphenychromone and allylamine afforded the desired amine as white needles, m.p. 119- (iPrOH); yield, 82%. Its hydrochloride salt had m.p. 140°–142° (iPrOH/PhCH$_3$); containing water).

Anal. Calc'd. for $C_{27}H_{25}NO_4$ (the free base): C, 75.85; H, 5.89; N, 3.27; O, 14.97.

Found: C, 75.87; H, 5.95; N, 3.14; O, 15.04.

EXAMPLE 5

Preparation of 7-(3-cyclopentylamino-2-hydroxypropoxy)-2,3-diphenylchromone hydrochloride Using Method B, the reaction of 7-(2,3-epoxypropoxy)-2,3-diphenylchromone and cyclopentylamine gave the title amine as white crystals; m.p. 162.5°–163° (iPrOH); yield 87%. Its hydrochloride salt was prepared as usual and melted at 155°–156° (iPrOH).

Anal. Calc'd. for $C_{29}H_{30}ClNO_4 \cdot 1\tfrac{1}{2}H_2O$: C, 67.11; H, 6.41; Cl, 6.83; N, 2.70; O, 16.95.

Found: C, 67.04; H, 5.90; Cl, 6.70; N, 2.66; O, 17.04.

EXAMPLE 6

Preparation of 7-(3-sec-butylamino-2-hydroxypropoxy)-2,3-diphenylchromone

The title compound was synthesized according to Method B, in 98% yield, as white crystals, m.p. 139°–139.5°.

Anal. Calc'd. for $C_{28}H_{29}NO_4$: C, 75.82; H, 6.59; N, 3.15.

Found: C, 75.50; H, 6.81; N, 3.10.

EXAMPLE 7

Preparation of 7-[3-(N-methyl-N-propylmino)-2-hydroxypropoxy]-2,3-diphenylchromone maleate Using Method B, the free base of the title compound was prepared from the corresponding epoxide and N-methylpropylamine. The obtained amine was dissolved in isopropyl alcohol and reacted with a solution of maleic acid in isopropyl alcohol. The white crystals formed were collected; m.p. 135°–137°.

Anal. Calc'd. for $C_{32}H_{33}NO_8$: C, 68.68; H, 5.94; N, 2.50.

Found: C, 68.88; H, 5.98; N, 2.26.

Pharmacology Data

Antihypertnsive activity was determined in the sponaneously hypertensive rat. Animals were dosed with compounds of Examples 1 to 7 or the control vehicle following a control blood pressure (systolic) and heart rate determinationmade by means of an inflatable tail cuff. Five animals per test group were employed. A decrease in systolic blood pressure which was statistically different from both the control animals and the pretreatment measurement is classified as significant activity.

The following table gives the minimum tested dosage producing significant activity at 5 hours for the compounds indicated.

| Example No | $R_1$, R | Minimum effective dosage tested (mg/kg) 5 hrs |
| --- | --- | --- |
| 1 | isopropyl, H | 8 |
| 2 | n-propyl, H | 35 |
| 3 | cyclopropyl, H | 17 |
| 4 | allyl, H | 75 |
| 5 | cyclopentyl, H | 75 |
| 6 | sec-butyl, H | 75 |
| 7 | n-propyl, methyl | 75 |

These compounds do not exhibit beta-blocking activity when determined as antagonism of isoproterenol-induced beta stimulation of isolated rat heart or inhibition of isoproterenol-induced effects on the cardiovascular system of the anesthetized rate.

What is claimed is:

1. Chromone having the formula

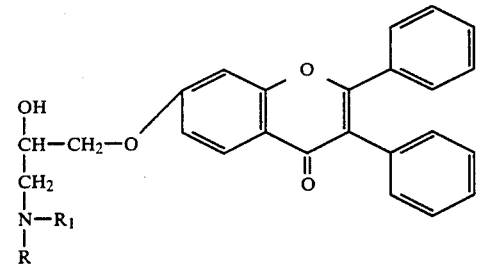

or a pharmaceutically acceptable salt thereof wherein R is hydrogen or lower alkyl, $R_1$ is hydrogen, lower alkyl, lower cycloalkyl or lower alkenyl.

2. The chomone of claim 1 wherein R is hydrogen and $R_1$ is i-propyl, n-propyl or cyclopropyl.

3. The chromone of claim 2 wherein $R_1$ is n-propyl.

4. The compound 7-(3-n-propylamino-2-hydroxypropoxy)-2,3-diphenylchromone hydrochloride.

5. The compound 7-[2-hydroxy-3-(isopropylamino)-propoxy]-2,3-diphenylchromone hydrochloride.

6. The compound 7-(3-cyclopropylamino-2-hydroxypropoxy)-2,3-diphenylchromone hydrochloride.

7. The compound 7-(3-allylamino-2-hydroxypropoxy)-2,3-diphenylchromone hydrochloride.

8. The compound 7-(3-cyclopentylamino-2-hydroxypropoxy)-2,3-diphenylchromone hydrochloride.

9. The compound 7-(3-sec-butylamino-2-hydroxypropoxy)-2,3-diphenylchromone hydrochloride.

10. The compound 7-[3-(N-methyl-N-propylamino)-2-hydroxypropoxy]-2,3-diphenylchromone maleate.